(12) United States Patent
Im et al.

(10) Patent No.: US 10,064,832 B2
(45) Date of Patent: Sep. 4, 2018

(54) KARTOGENIN-CONJUGATED CHITOSAN PARTICLES WITH IMPROVED SUSTAINED RELEASE PROPERTY AND BIOCOMBATIBILITY, AND USE THEREOF

(71) Applicant: DONGGUK UNIVERSITY INDUSTRY-ACADEMY COOPERATION FOUNDATION, Seoul (KR)

(72) Inventors: Gun Il Im, Gyeonggi-do (KR); Mi Lan Kang, Seoul (KR)

(73) Assignee: DONGGUK UNIVERSITY INDUSTRY-ACADEMY COOPERATION FOUNDATION (KR)

( * ) Notice: Subject to any disclaimer, the term of this patent is extended or adjusted under 35 U.S.C. 154(b) by 0 days.

(21) Appl. No.: 15/505,980

(22) PCT Filed: Aug. 11, 2015

(86) PCT No.: PCT/KR2015/008410
§ 371 (c)(1),
(2) Date: Feb. 23, 2017

(87) PCT Pub. No.: WO2016/032148
PCT Pub. Date: Mar. 3, 2016

(65) Prior Publication Data
US 2017/0290791 A1    Oct. 12, 2017

(30) Foreign Application Priority Data
Aug. 26, 2014    (KR) ..................... 10-2014-0111572

(51) Int. Cl.
| A61K 31/167 | (2006.01) |
| A61K 9/00 | (2006.01) |
| A61K 47/48 | (2006.01) |
| A61K 31/722 | (2006.01) |
| C08B 37/08 | (2006.01) |
| C08L 5/08 | (2006.01) |
| A61K 47/69 | (2017.01) |

(52) U.S. Cl.
CPC .......... *A61K 31/167* (2013.01); *A61K 9/0019* (2013.01); *A61K 31/722* (2013.01); *A61K 47/48923* (2013.01); *A61K 47/6927* (2017.08); *A61K 47/6939* (2017.08); *C08B 37/003* (2013.01); *C08L 5/08* (2013.01)

(58) Field of Classification Search
None
See application file for complete search history.

(56) References Cited

U.S. PATENT DOCUMENTS

| 7,459,307 B2 | 12/2008 | Ha et al. |
| 8,546,529 B2 | 10/2013 | Chung et al. |

FOREIGN PATENT DOCUMENTS

| KR | 10-0494265 B1 | 6/2005 |
| KR | 2008-0107198 A | 12/2008 |
| KR | 2012-0052116 A | 5/2012 |
| KR | 2014-0090481 A | 7/2014 |

OTHER PUBLICATIONS

Kang, Biomaterials 35 (2014) 9984-9994.*
Zhang et al., (2012) "Micro- and Nano-Carrier Mediated Intra-Articular Drug Delivery Systems for the Treatment of Osteoarthritis" Journal of Nanotechnology, vol. 2012, Article ID 748909, pp. 2-13.
Mobasheri (2013) "The Future of Osteoarthritis Therapeutics: Emerging Biological Therapy" Curr Rheumatol Rep vol. 15:385, pp. 2-10.

* cited by examiner

*Primary Examiner* — Layla D Berry
(74) *Attorney, Agent, or Firm* — Riverside Law LLP

(57) ABSTRACT

The present invention relates to kartogenin-conjugated chitosan particles with an improved sustained release property and biocompatibility. Effects of increases in biocompatibility, chondrogenic differentiation efficiency and retention time in the joints were confirmed by using kartogenin-chitosan microparticles or kartogenin-chitosan nanoparticles of the present invention, and thus targeted treatment, in the prevention or treatment of bone diseases, is enabled through a more fundamental approach.

7 Claims, 20 Drawing Sheets

KARTOGENIN-CONJUGATED CHITOSAN PARTICLES WITH IMPROVED SUSTAINED RELEASE PROPERTY AND BIOCOMBATIBILITY, AND USE THEREOF

STATEMENT REGARDING GOVERNMENT RIGHTS

The present invention was undertaken with the support of 1) Development of gene vector and animal model for the cell therapy of osteoarthritis No. 1465018079 grant funded by the Ministry of Health & Welfare, 2) Development of drug delivery systems of intra-articular injection for the cartilage regeneration of osteoarthritis No. 2013R1A1A2062978 grant funded by the Ministry of Science, ICT and Future Planning, and 3) Reconstruction and modulation of artificial stem cell niche for iPSCs using nanotopography No. 2015R1A2A1A09002793 grant funded by the Ministry of Science, ICT and Future Planning.

CROSS-REFERENCE TO RELATED APPLICATIONS

This application claims priority to and the benefit of Korean Patent Application No. 10-2014-0111572, filed on Aug. 26, 2014 and International Patent Application No. PCT/KR2015/008410, filed on Aug. 11, 2015, the disclosure of which is incorporated herein by reference in its entirety.

TECHNICAL FIELD

The present invention relates to kartogenin-conjugated chitosan particles with an improved sustained release property and biocompatibility, and more particularly, to a kartogenin-chitosan composite formed by a covalent bond between kartogenin which is a hydrophobic compound and chitosan which is a hydrophilic compound.

BACKGROUND ART

In general, once cartilage tissue that forms the joints of vertebrates is damaged, the cartilage tissue is very difficult to normally regenerate in vivo. When the cartilage tissue of the joints is damaged, a patient feels severe pain and the patient's daily activities may be limited. Further, when chronic, degenerative arthritis or the like can lead to fatal complications, and the normal life or professional activity of the patient is hindered, thereby greatly affecting the daily lives of modern people.

This cartilage damage occurs at a high frequency due to osteoarthritis causing traumatic defects or the gradual destruction of articular cartilage tissue. Thus, studies on a method of treating osteoarthritis have been conducted, for example, chondroplasty, osteochondral transplantation, autologous chondrocyte transplantation and the like have been performed, but in the case of surgery of a relatively young patient under 60 years old, there is a problem in terms of the lifespan of artificial joints.

Furthermore, although a local injection therapy of directly injecting steroid agents or hyaluronic acid into the joints has been widely used, while these anti-inflammatory drugs have an effect of alleviating symptoms, weakened cartilage and systemic side effects may be caused and damaged cartilage cannot be generated, and thus the local injection therapy using anti-inflammatory drugs cannot be a fundamental treatment. Therefore, when drugs capable of inducing regeneration of cartilage in the osteoarthritic region are applied to the local injection therapy, the effect of the treatment may be enhanced.

Recently, kartogenin has been reported as a drug that can induce chondrogenic differentiation of adult mesenchymal stem cells, and it was determined from animal experiments with mice that kartogenin triggers the activity of mesenchymal stem cells in cartilage to generate chondrocytes, thereby recovering damaged cartilage. However, since a kartogenin compound has a very low molecular weight, is water-insoluble and exhibits hydrophobic properties, there is a limit in application thereof as a drug.

Moreover, in terms of a method of administration of a drug for treating osteoarthritis, a method of intra-articular injection is a treatment method showing the highest expected effect due to directly injecting drugs into damaged joints. However, since drugs in a liquid state injected into the joints are quickly dispersed and the retention time thereof in the joints is too short, it is necessary to increase the concentration of drugs or the number of doses, but this may rather lead to systemic side effects.

Therefore, for local intra-articular injection for the effective treatment of osteoarthritis, studies on a composite that not only improves the biocompatibility of hydrophobic drugs such as kartogenin and also enables continuous drug release have been carried out (Korean Patent Publication No. 10-2014-0090481), but it remains inadequate.

DISCLOSURE

Technical Problem

In view of the above-described problems, Kartogenin-Chitosan micro/nanoparticles effects of increasing biocompatibility, chondrogenic differentiation efficiency and retention time in the joints were identified and the present invention has been completed based on the identification by the inventors of the present invention.

The present invention provides a Kartogenin-conjugated chitosan particle formed by a covalent bond between kartogenin which is a hydrophobic compound and chitosan which is a hydrophilic compound.

Further, the present invention also provides a pharmaceutical composition for preventing or treating bone diseases, which includes kartogenin-conjugated chitosan particles.

However, the scope of the present invention is not limited to the above-described objects, and other unmentioned objects may be clearly understood by those skilled in the art from the following description.

Technical Solution

In view of the above-described objects, the present invention provides a kartogenin-conjugated chitosan particle formed by a covalent bond between kartogenin which is a hydrophobic compound and chitosan which is a hydrophilic compound.

In one implementation example of the present invention, the covalent bond forming the kartogenin-conjugated chitosan particle may be a peptide bond.

In another implementation example of the present invention, the kartogenin-conjugated chitosan particle may be in the form of a nanoparticle or a microparticle.

The present invention also provides a pharmaceutical composition for preventing or treating bone diseases, containing the kartogenin-conjugated chitosan particle as an active ingredient.

In one implementation example of the present invention, the bone disease may be osteoarthritis.

In another implementation example of the present invention, the pharmaceutical composition may be an injectable formulation for intra-articular administration.

The present invention also provides a method for treating bone diseases, including a step of administering the pharmaceutical composition to a subject.

The present invention also provides a use of treating bone diseases with the composition containing the kartogenin-conjugated chitosan particles Advantageous Effects The present invention relates to kartogenin-conjugated chitosan particles with an improved sustained release property and biocompatibility. Kartogenin-chitosan microparticles or kartogenin-chitosan nanoparticles are prepared using the kartogenin-conjugated chitosan particles, and effects of increasing biocompatibility, chondrogenic differentiation efficiency, retention time in the joints, preventing arthritis progression and treating arthritis were identified. Accordingly, the composition is expected to be beneficially used as a pharmaceutical composition such as an injectable formulation for intra-articular administration or the like for the prevention or treatment of bone diseases.

MODES OF THE INVENTION

Figure 1:
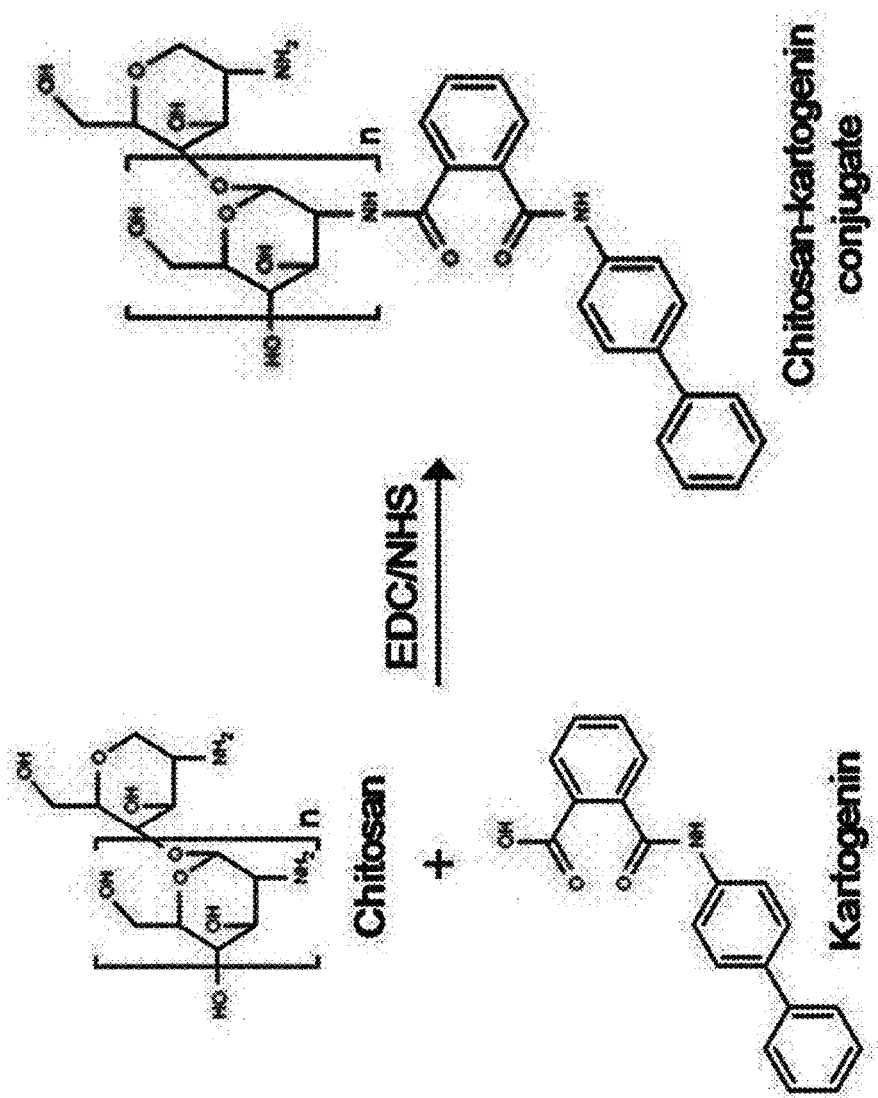
FIG. 1 is a diagram schematically illustrating a chemical formula for a synthesis reaction of kartogenin-conjugated chitosan particles.

The inventors of the present invention synthesized kartogenin-conjugated chitosan particles by inducing a covalent bond between kartogenin and chitosan, and prepared kartogenin-chitosan microparticles or kartogenin-chitosan nanoparticles using these kartogenin-conjugated chitosan particles. Furthermore, non-cytotoxicity and non-inflammatory properties were confirmed from groups each treated with the kartogenin-chitosan microparticles or kartogenin-chitosan nanoparticles, and high chondrogenic differentiation efficiency, an increase in retention time in the joints and excellent cartilage regeneration effects were also identified therefrom as compared to a group treated with kartogenin only, and thereby the present invention has been completed based on the identification.

Hereinafter, the present invention will be described in detail.

The present invention provides a kartogenin-conjugated chitosan particle formed by a covalent bond between kartogenin which is a hydrophobic compound and chitosan which is a hydrophilic compound.

As used herein, the term "kartogenin" refers to a compound that promotes the regeneration of damaged cartilage by triggering the activity of mesenchymal stem cells in the cartilage to generate chondrocytes, and differentiation from mesenchymal stem cells into chondrocytes has been confirmed in a test where degenerative arthritis model rats are used. However, kartogenin has a problem in terms of solubility and biocompatibility due to having a low molecular weight and hydrophobicity. Thus, in the present invention, kartogenin-conjugated chitosan particles having an improved sustained release property and biocompatibility are provided by covalent bonding of hydrophobic kartogenin to hydrophilic chitosan, and preferably, the kartogenin-conjugated chitosan particles may be in the form of nanoparticles or microparticles, but are not limited thereto.

Accordingly, the present invention provides kartogenin-conjugated chitosan particles prepared by binding with chitosan which is a hydrophilic compound. The chemical bond between kartogenin and chitosan is a covalent bond, and preferably, may be a peptide bond.

In the present invention, a method using a polymer-drug composite with a covalent bond is distinctive from a method of encapsulating drugs in polymeric structures or the like which is a conventional drug delivery system, and induces a covalent bond between kartogenin which is a hydrophobic compound and chitosan which is a hydrophilic compound to increase the solubility and biocompatibility of kartogenin.

In one embodiment of the present invention, kartogenin-conjugated chitosan particles were synthesized (see Example 1), kartogenin-chitosan micro/nanoparticles using the kartogenin-conjugated chitosan particles were prepared to identify continuous drug release of kartogenin in a test tube (see Examples 2 and 3), and non-cytotoxicity and non-inflammatory properties of the micro/nanoparticles were confirmed (see Example 4). Furthermore, increases in the expression levels of COL2 and AGC which are chondrogenic differentiation factors and a decrease in an expression level of collagenage type X which is a cartilage hypertrophy factor were confirmed (see Example 5), an increase in retention time in the joints (see Example 6) and the promotion of the regeneration of cartilage (see Example 7) were identified from osteoarthritis animal models, and thus it was confirmed that the kartogenin-conjugated chitosan particles can be usefully used as a pharmaceutical composition for treating or preventing bone diseases.

Therefore, a pharmaceutical composition for preventing or treating bone diseases which contains kartogenin-conjugated chitosan particles as an active ingredient is provided.

As used herein, the term "preventing" refers to all actions that inhibit bone diseases or delay the development of the bone diseases by administering the pharmaceutical composition according to the present invention.

As used herein, the term "treating" refers to all actions that alleviate or beneficially change the condition of bone diseases by administering the pharmaceutical composition according to the present invention.

Bone diseases to be prevented or treated in the present invention denote conditions or diseases requiring an increase in bone mass by the promotion of osteoblast activity, include diseases with bone mass loss, and preferably, may be osteoarthritis, but is not limited thereto.

The pharmaceutical composition according to the present invention may include a pharmaceutically acceptable carrier in addition to the active ingredient. Here, the pharmaceutically acceptable carrier is typically used in the formulation, and examples thereof include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrups, methyl cellulose, methylhydroxybenzoate, propylhydroxybenzoate, talc, magnesium stearate, and mineral oil, but are not limited thereto. The pharmaceutical composition of the present invention may further include lubricants, wetting agents, sweeteners, aromatics, emulsifiers, suspensions, and preservatives besides the above components.

The pharmaceutical composition according to the present invention may be administered orally or parenterally (e.g., intravenously, subcutaneously, intraperitoneally, or locally) according to the desired method, and preferably, may be administered intra-articularly by an injectable formulation. The composition according to the present invention can both stay in the joints for a long time and release drugs continuously as compared to a conventional injectable formulation for intra-articular administration for treating bone diseases, and thus can be an effective treatment method for bone diseases.

The pharmaceutical composition of the present invention is administered in a pharmaceutically effective amount. The dose of the pharmaceutical composition may vary depending on a patient's condition and body weight, severity of a disease, a dosage form, administration route and duration, and may be suitably selected by those skilled in the art. As used herein, the term "pharmaceutically effective amount" refers to an amount sufficient to treat diseases, at a reasonable benefit/risk ratio applicable to any medical treatment. The effective dosage level of the pharmaceutical composition may be determined depending on the subject's type, the disease severity, the subject's age and sex, the type of the disease with bone mass loss, the activity of the drug, sensitivity to the drug, the time of administration, the route of administration, excretion rate, the duration of treatment, factors including drugs used in combination with the composition, and other factors known in the medical field. The pharmaceutical composition of the present invention may be administered alone or in combination with other therapeutic agents, and may be administered sequentially or simultaneously with conventional therapeutic agents. The pharmaceutical composition can be administered in a single dose or multiple doses. It is important to administer the pharmaceutical composition at the minimum amount that can exhibit the maximum effect without causing side effects, in view of all the above-described factors, and this amount can be easily determined by those skilled in the art.

Specifically, an effective amount of the pharmaceutical composition of the present disclosure may be determined by a patient's age, sex, condition, weight, absorption rate of an active ingredient in the body, inactivation rate and excretion rate, the type of a disease, or a co-administered drug. Generally, the composition may be administered at 0.001 to 150 mg, and preferably, 0.01 to 100 mg per 1 kg of body weight, daily or every other day, or once to three times a day. Especially, when the composition is administered intra-articularly as an injectable formulation, 0.7 mg of kartogenin-chitosan nanoparticles per 1 kg of body weight and 8 mg of kartogenin-chitosan microparticles per 1 kg of body weight may be administered twice at intervals of 3 weeks, but are not limited thereto. Moreover, the effective amount may vary depending on an administration route, the severity of a bone disease, sex, body weight or age of a patient, and therefore, it should be noted that the present invention is not limited by varying the dose.

According to another aspect of the present invention, the present invention provides a method for treating bone diseases that includes a step of administering the pharmaceutical composition to a subject. As used herein, the term "subject" refers to a subject having a disease to be treated, and more specifically, mammals such as humans or non-human primates, mice, rats, dogs, cats, horses, cattle, etc.

Hereinafter, exemplary examples of the invention will be described for promoting an understanding of the invention. However, the following examples should be considered in a descriptive sense only and the scope of the invention is not limited to the following examples.

Example 1. Preparation and Identification of Kartogenin-Conjugated Chitosan Particles For synthesis of kartogenin-conjugated chitosan particles, the formation of a covalent bond between a carboxyl group of kartogenin and an amine group of chitosan was induced using EDC/NHS (ethyl(dimethylaminopropyl)carbodiimide/N-Hydroxysuccinimide) which is a reactive derivative. Kartogenin at the proper molar ratio was reacted with the EDC/NHS reactive derivative at 25° C. for one hour, and then added to a low molecular weight chitosan (50-190 kDa) or medium molecular weight chitosan (190-310 kDa) solution dissolved in a 1% (volume/volume) acetic acid solvent and stirred for 24 hours at a low speed. Unbound kartogenin, chitosan and EDC/NHS were removed by dialysis and lyophilized. In order to confirm the formation of a covalent bond, Fourier Transform Infrared spectrophotometer (FT-IR) and Proton Nuclear Magnetic Resonance spectroscopy ($^1$H-NMR) analyses were carried out.

Figure 2:
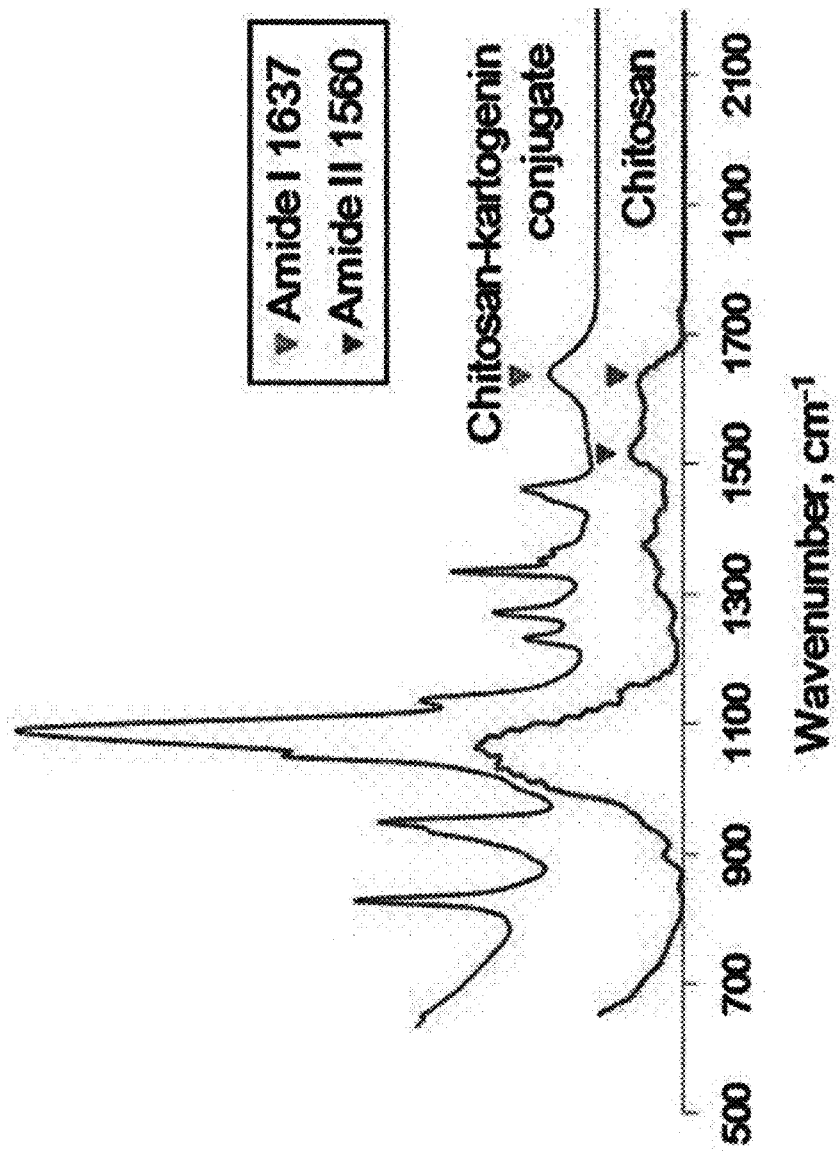
FIG. 2 shows the identification result of a covalent bond of kartogenin-conjugated chitosan particles by Fourier transform infrared spectroscopy (FT-IR).
Figure 3A:
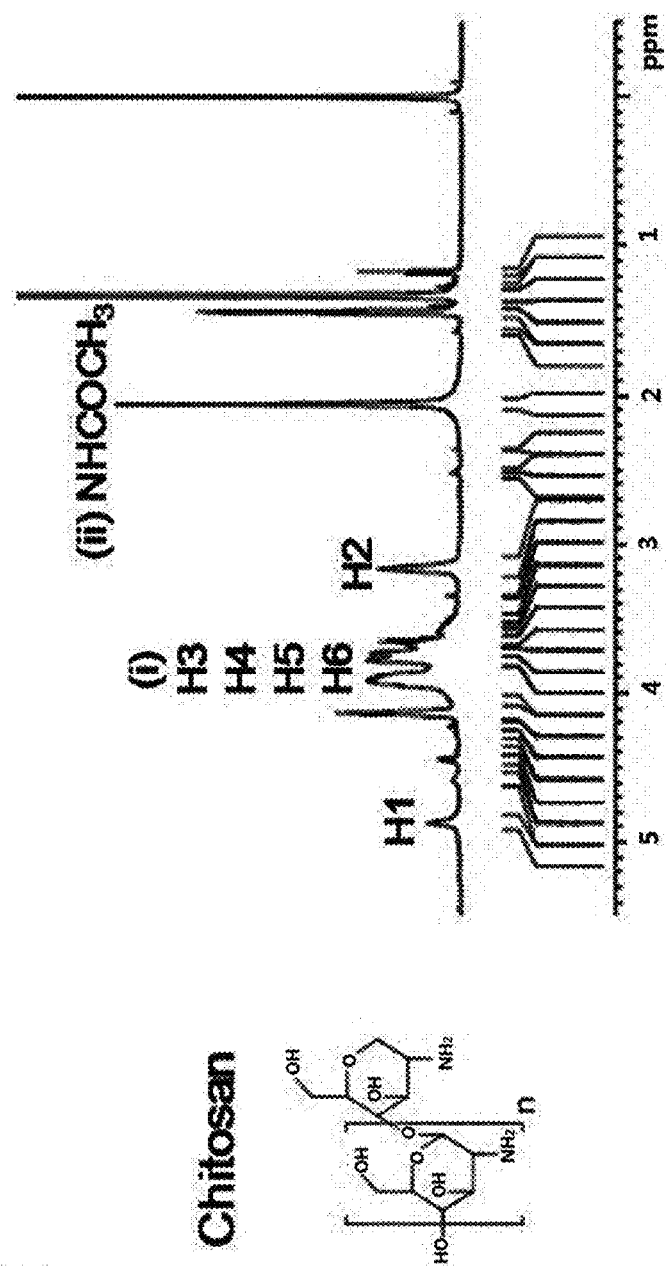
FIG. 3A shows the identification result of chitosan by Proton Nuclear Magnetic Resonance spectroscopy ($^1$H-NMR).
Figure 3B:
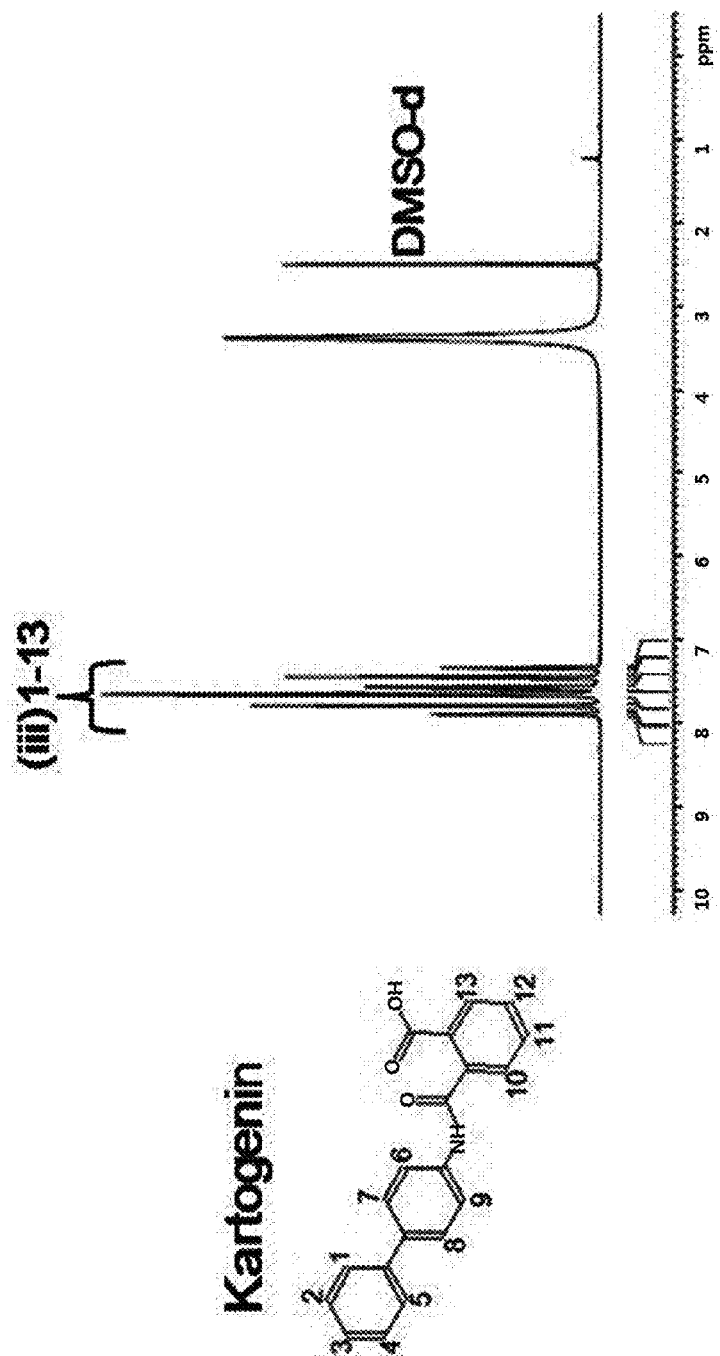
FIG. 3B shows the identification result of kartogenin by $^1$H-NMR.
Figure 3C:
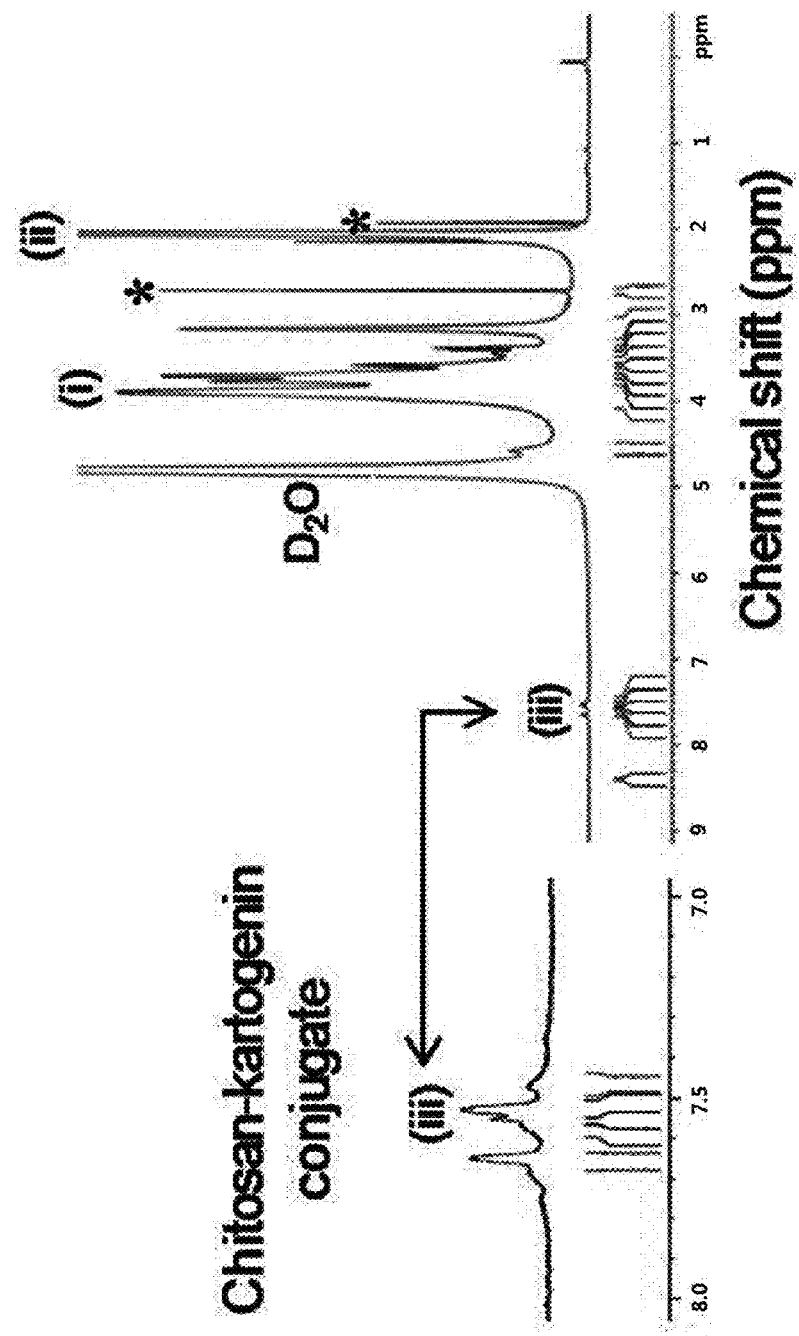
FIG. 3C shows the identification result of a covalent bond of kartogenin-conjugated chitosan particles by $^1$H-NMR.

As shown in FIG. 2, it was identified from FT-IR analysis that the second amine group having a weaker N—H bond than a strong N—H bond of the first amine group of chitosan formed a covalent bond with a carboxyl group of kartogenin and lost an inherent amide bond. Also, as shown in FIG. 3, a covalent bond was confirmed from resonance peaks ($\delta$7.5-8) indicating hydrogen of the benzene ring of kartogenin and resonance peaks ($\delta$1.9/$\delta$2.7) of hydrogen of a methyl (—CH$_3$)/methylene (—CH$_2$) group positioned at C2 of chitosan in $^1$H-NMR analysis.

Example 2. Preparation of Kartogenin-Chitosan Micro/Nanoparticles

Kartogenin-chitosan micro/nanoparticles were prepared by an ionic gelation method using tripolyphosphate. In the case of microparticles, kartogenin-medium molecular weight chitosan composite particles were dissolved in a 1% acetic acid solution at a concentration of 0.85% (weight/volume), and mixed with tripolyphosphate dissolved in deionized water at a mass ratio of 4:1 (kartogenin-low molecular weight chitosan composite particles:tripolyphosphate), and then stirred at 700 rpm for 10 minutes. In the case of nanoparticles, kartogenin-low molecular weight chitosan composite particles were dissolved in a 1% acetic acid solution at a concentration of 0.05% (weight/volume), mixed with tripolyphosphate dissolved in deionized water at a mass ratio of 2:1 (kartogenin-low molecular weight chitosan composite particles:tripolyphosphate), and then stirred at 700 rpm for 10 minutes. The prepared kartogenin-chitosan micro/nanoparticles were centrifuged at 15000 rpm for 20 minutes and lyophilized. The morphologies of the kartogenin-chitosan micro/nanoparticles was confirmed by Scanning Electron Microscopy (SEM), and the sizes of the micro/nanoparticles was analyzed with a Dynamic Light Scattering spectrophotometer (DLS).

Figure 4A:
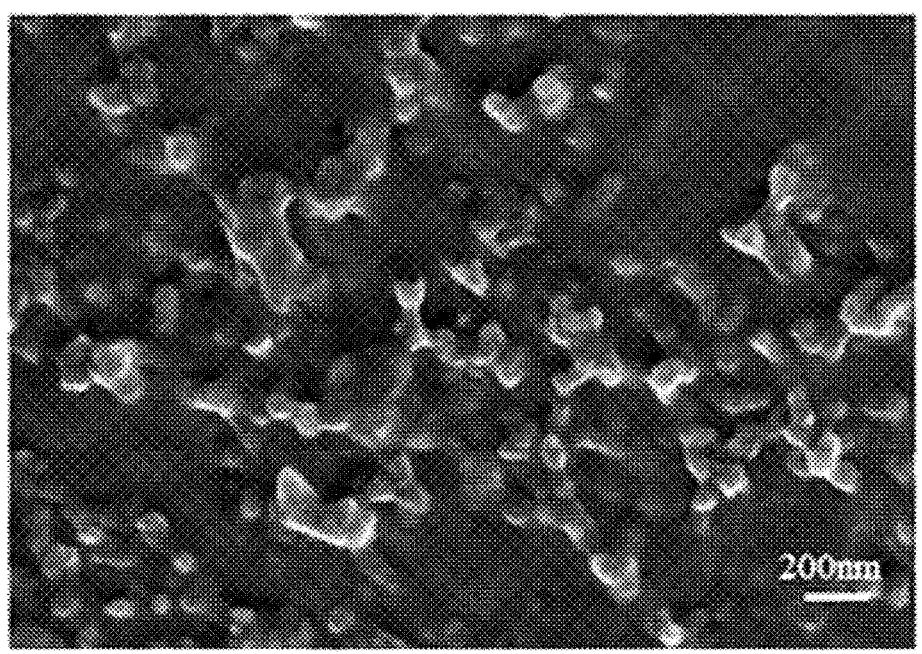
FIG. 4A shows the identification result of the morphology of kartogenin-chitosan microparticles by Scanning Electron Microscopy (SEM).
Figure 4B:
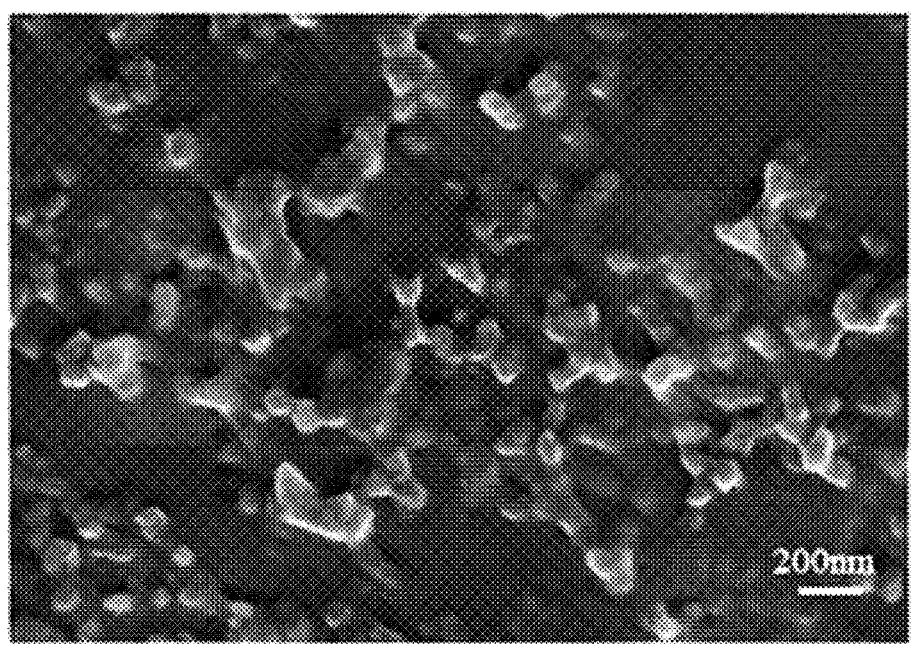
FIG. 4B shows the identification result of the morphology of kartogenin-chitosan nanoparticles by SEM.

As shown in FIG. 4, the morphologies of the microparticles prepared using kartogenin-medium molecular weight chitosan composite particles and nanoparticles prepared using kartogenin-low molecular weight chitosan composite particles were identified, and kartogenin-chitosan microparticles showed a size distribution of 1.8±0.54 μm, and kartogenin-chitosan nanoparticles showed a size distribution of 150±39 nm.

Example 3. Experiment of Drug Release of Kartogenin-Chitosan Micro/Nanoparticles After each of 100 mg of kartogenin-chitosan micro/nanoparticles were suspended in 1 mL of PBS and reacted at 37° C., centrifugation was conducted at 15,000 rpm for 20 minutes to eliminate a supernatant, and kartogenin released from the kartogenin-chitosan micro/nanoparticles was dissolved in ethanol. Subsequently, ethanol was removed by centrifugation performed at 15,000 rpm for 20 minutes, and was replaced with 1 mL of new PBS, and the process was repeated once a day. The content of kartogenin released from the kartogenin-chitosan micro/nanoparticles was analyzed by high-performance liquid chromatography (HPLC).

Figure 5A:
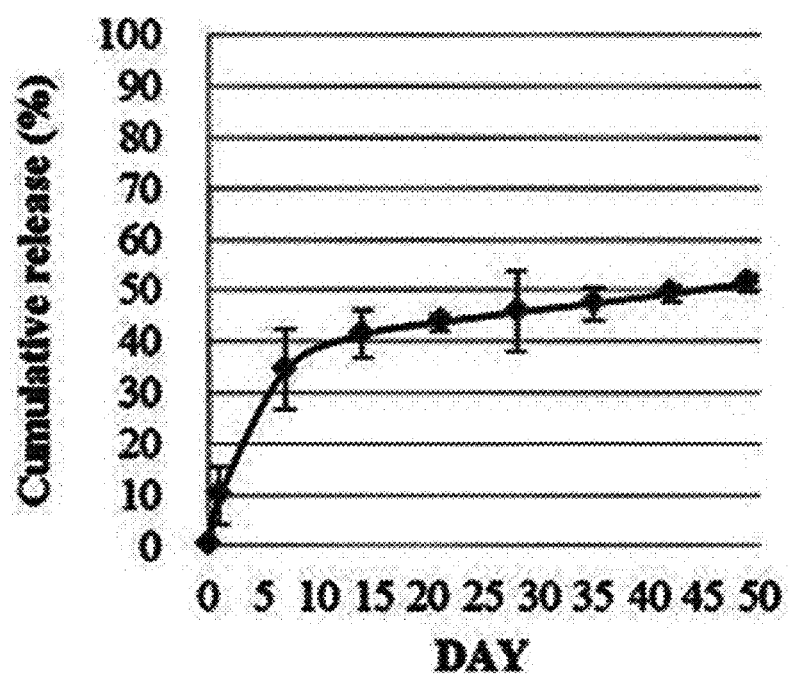
FIG. 5A shows the identification result of the release amount of kartogenin-chitosan microparticles in a test tube by high-performance liquid chromatography (HPLC).
Figure 5B:
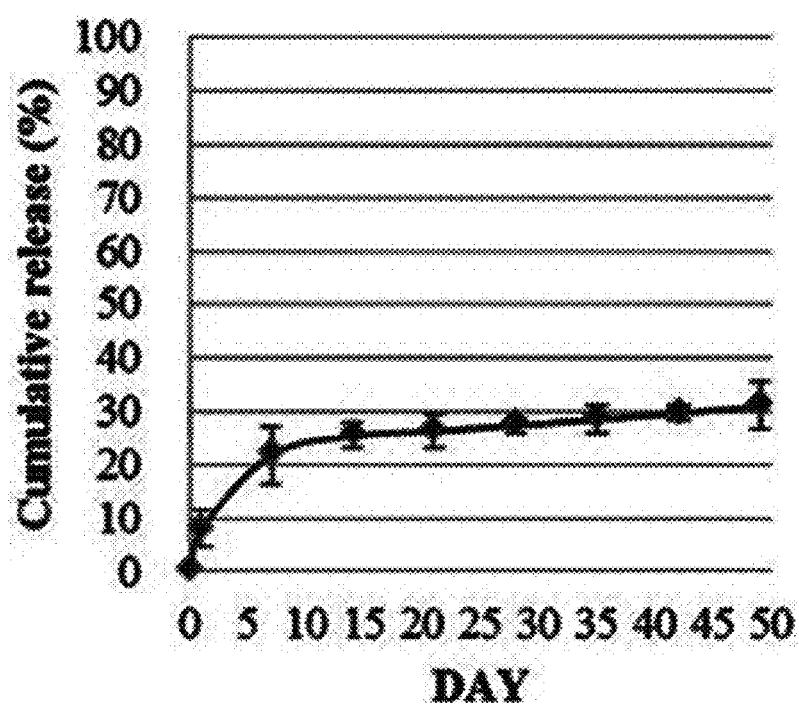
FIG. 5B shows the identification result of the release amount of kartogenin-chitosan nanoparticles in a test tube by HPLC.

As shown in FIG. 5, it was identified that 50% or less of kartogenin was released from the kartogenin-chitosan microparticles, until week 6, and less than 30% of kartogenin was released from the kartogenin-chitosan nanoparticles, until week 7, and thus it was confirmed that nanoparticles enable continuous drug release for a longer time than microparticles. As a result, the drug delivery system of kartogenin-chitosan micro/nanoparticles prepared in the examples was determined to stably deliver kartogenin for a long period of 6 to 7 weeks or more to allow continuous drug release in the body.

Example 4. Cytotoxicity Test and Inflammatory Response Inducibility Test of Kartogenin-Chitosan Micro/Nanoparticles The cytotoxicity potential of kartogenin-chitosan microparticles was evaluated from bone marrow mesenchymal stem cells by a Microculture Tetrazolium (MTT) assay. Bone marrow mesenchymal stem cells ($1\times10^4$ cells/well) were cultured in a 96-well plate, and treated with kartogenin-chitosan micro/nanoparticles that can secrete 1, 10, 100 and 1000 nM of kartogenin, respectively. After 1, 4 and 7 days, bone marrow mesenchymal stem cells were treated with 50 μL of an MTT solution and cultured for 3 hours, and then the MTT solution was removed. 150 μL of a DMSO solution was aliquoted therein and a reaction was performed for 10 minutes, and absorbance was measured at 570 nm. Furthermore, the inflammatory response inducibility of kartogenin-chitosan micro/nanoparticles in cells was determined by measuring the secretion amount of IL-6 which is an inflammatory cytokine. Chondrocytes ($1\times10^5$ cells/well) were cultured in a 6-well plate and respectively treated with 1 µg/well of Lipopolysaccharides (LPS), kartogenin, kartogenin-chitosan microparticles and kartogenin-chitosan nanoparticles. The culture solution was collected over time and the secreted IL-6 was quantified using an enzyme-linked immunoabsorbent assay (ELISA).

Figure 6A:
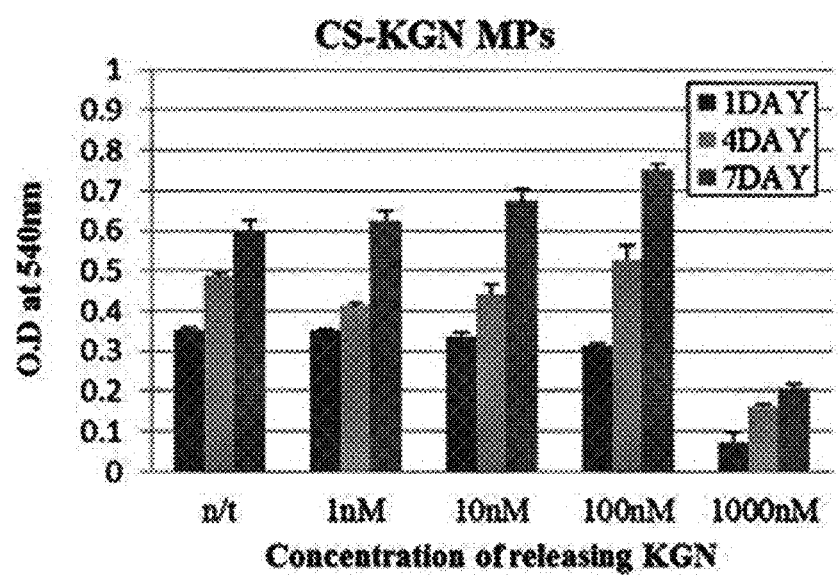
FIG. 6A shows the evaluation result of cytotoxicity of kartogenin-chitosan microparticles by a Microculture Tetrazolium (MTT) assay.
Figure 6B:
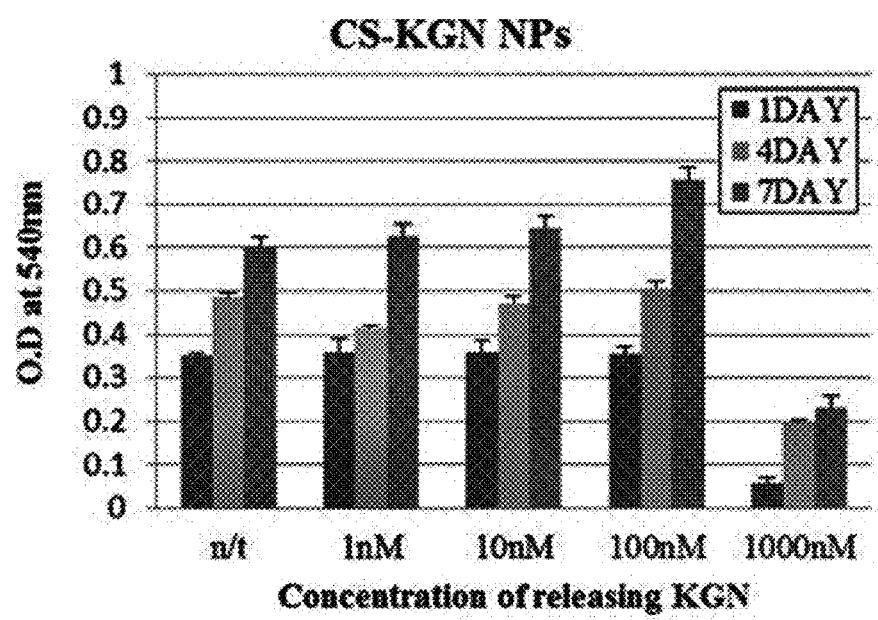
FIG. 6B shows the evaluation result of cytotoxicity of a group treated with kartogenin-chitosan nanoparticles by the MTT assay.

As shown in FIG. 6, when cells were treated with kartogenin-chitosan microparticles or kartogenin-chitosan nanoparticles that can secrete 100 nM or less (1 nM, 10 nM and 100 nM) of kartogenin for a week, no cytotoxicity was identified.

Figure 7:
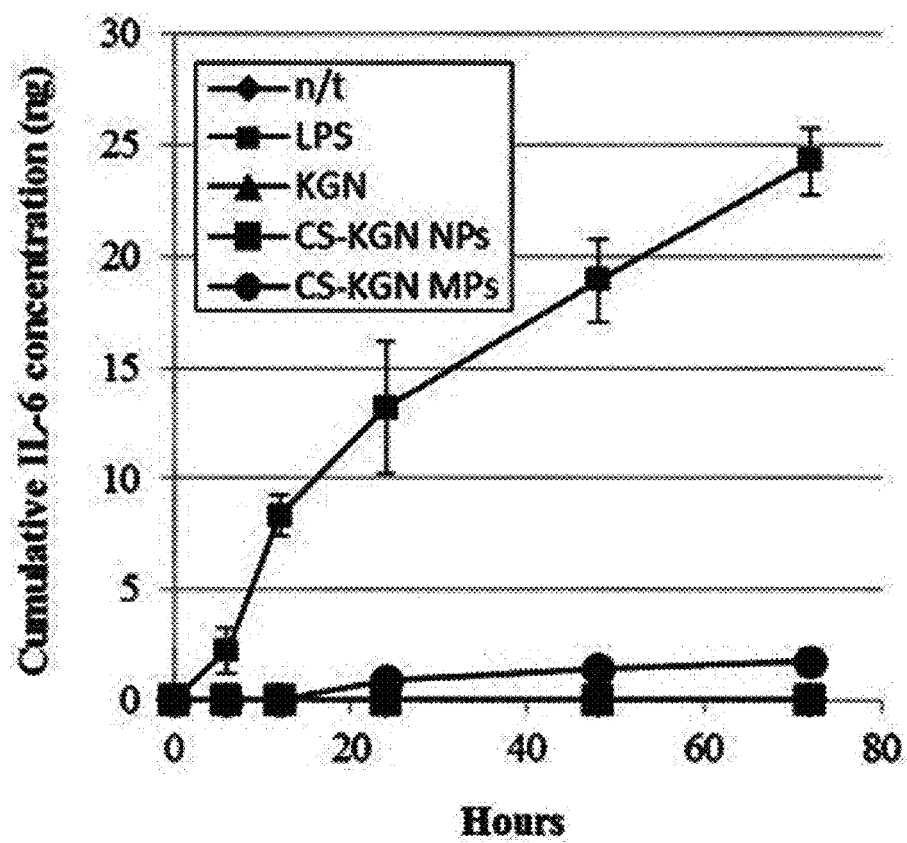
FIG. 7 shows the identification result of the secretion amount of IL-6 of groups each treated with kartogenin-chitosan microparticles and kartogenin-chitosan nanoparticles (LPS: a group treated with lipopolysaccharides, KGN: a group treated with kartogenin only, CS-KGNNPs: a group treated with kartogenin-chitosan nanoparticles, CS-KGNMPs: a group treated with kartogenin-chitosan microparticles).

Further, as shown in FIG. 7, it was determined that a group treated with kartogenin-chitosan microparticles or kartogenin-chitosan nanoparticles showed almost no secretion of IL-6 like a negative control group that was not treated with anything while a group treated with bacterial Lipopolysaccharides (LPS) induced high secretion of IL-6 as a positive control group. Consequently, it was determined that the drug delivery system of kartogenin-chitosan micro/nanoparticles prepared in the examples is capable of delivering drugs without cytotoxicity at a concentration at which 100 nM or less of kartogenin can be secreted, and no inflammatory response is induced when being used as a drug delivery system, and thus has excellent biocompatibility.

Example 5. Analysis of Chondrogenic Differentiation Efficiency of Kartogenin-Chitosan Micro/Nanoparticles Bone marrow mesenchymal stem cells which were cultured in the form of pellets were transferred to a lower-layer well of a Transwell plate, and an upper-layer well on which membranes with a pore size of 0.1 µm were laid down was treated with kartogenin-chitosan micro/nanoparticles that can secret 100 nM of kartogenin, respectively. After 3 weeks, the well was treated with TRIzol (Invitrogen Co.) to separate RNA, and reverse transcription was performed using a Maxime RT preMix kit oligo (dT) primer (iNtRon Biotechnology). Then, the gene expression levels of collagen type II (COL2A1), aggrecan, collagen type I (COL1A1), SOX9 (sex determining region Y (SRY)-box 9) and Glyceraldehyde-3-phosphatedehydrogenase (GAPDH) were quantified by real-time polymerase chain reaction and compared with the expression level of GAPDH which is a housekeeping gene, and relatively quantified.

After 4 weeks of chondrogenic differentiation, pellets were collected and total proteins were separated using an RIPA lysis buffer (Thermo Scientific). The proteins were subjected to 8% SDS-polyacrylamide gel electrophoresis (SDS-PAGE), and blotted on a polyvinylidene fluoride (PVDF) membrane, 5% (v/w) skim milk was added to PBS including 0.05% (volume/volume) Tween 20, and then the membrane on which proteins were blotted was reacted for one hour. Primary antibodies of collagen type II (COL2A1), aggrecan, collagen type X (COL10A1), SOX9 (sex determining region Y (SRY)-box 9) and Glyceraldehyde-3-phosphatedehydrogenase (GAPDH) were reacted at 4° C. overnight, and secondary antibodies labeled with horseradish peroxidase were treated at room temperature for one hour. An image of signals emitted by a chemiluminescence (ECL) Western blotting detection reagent (Amersham Biosciences) was obtained using LAS-3000 (Fujifilm).

After 3 weeks of chondrogenic differentiation, pellets were collected and fixed in a 4% paraformaldehyde solution, and a block was prepared using paraffin wax. Pellets were cut to 4-µm sections and attached to a glass slide, and sections deparaffinized by xylene and ethanol were treated with a Safranin-O (0.1% weight/volume in distilled water) solution for 5 minutes, and treated with an alcian blue (1% weight/volume in 3% volume/volume acetic acid) solution for 30 minutes respectively, and washed with running water.

After 4 weeks of chondrogenic differentiation, pellets were collected and total DNA were separated using a GeneAll Tissue SV Mini Kit (GeneAll) and quantified by a nanophotometer (Implen). In order to separate a glycosaminoglycan (GAG), pellets immersed in a papain solution were treated at 60° C. for two hours, and added with a 1,9-dimethylmethylene blue (DMMB) assay buffer to be reacted for 30 minutes. A sulfated-GAG-dye complex was centrifuged at 15,000 rpm for 20 minutes, and re-suspended in a dye dissociation buffer, and then absorbance was measured at 656 nm. The amount of the glycosaminoglycan was relatively quantified as compared to the absorbance of a reference glycosaminoglycan with a known concentration, and divided by total DNA values for comparison.

Figure 8:
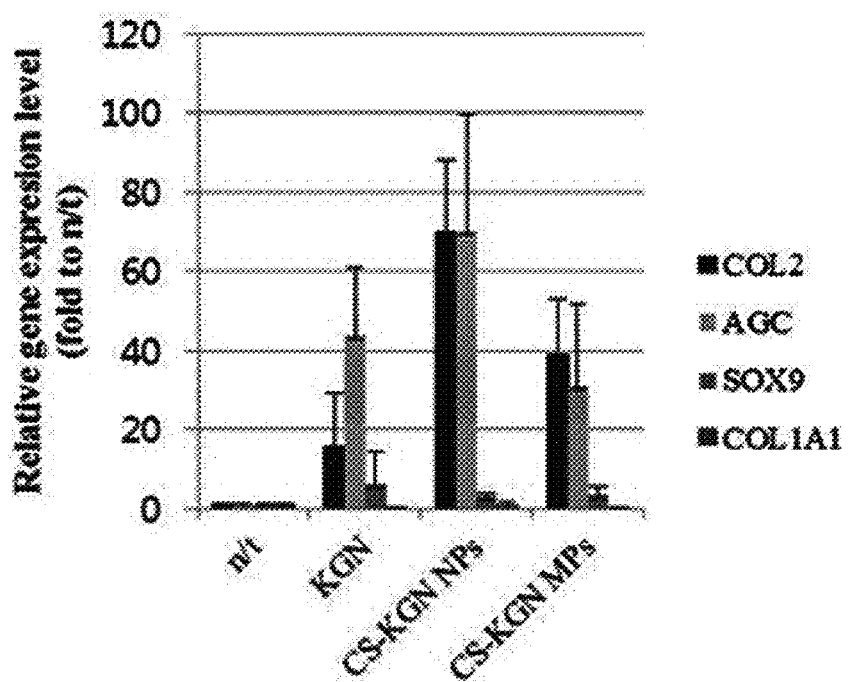
FIG. 8 shows the identification result of changes in expression levels of collagenase type II (COL2) and aggrecan (AGC) of groups each treated with kartogenin-chitosan microparticles and kartogenin-chitosan nanoparticles (KGN: a group treated with kartogenin only, CS-KGNNPs: a group treated with kartogenin-chitosan nanoparticles, CS-KGNMPs: a group treated with kartogenin-chitosan microparticles).

As shown in FIG. 8, it was confirmed that the expression of collagenase type II (COL2) and Aggrecan (AGC) which are chondrogenic differentiation factors increased 30-fold or more as compared to a control group, and especially, a group treated with kartogenin-chitosan nanoparticles showed a gene expression rate of COL2 which was three times higher than that of a group treated with kartogenin in a liquid state, and the gene expression rate of AGC was also increased 1.5-fold or more.

Figure 9:
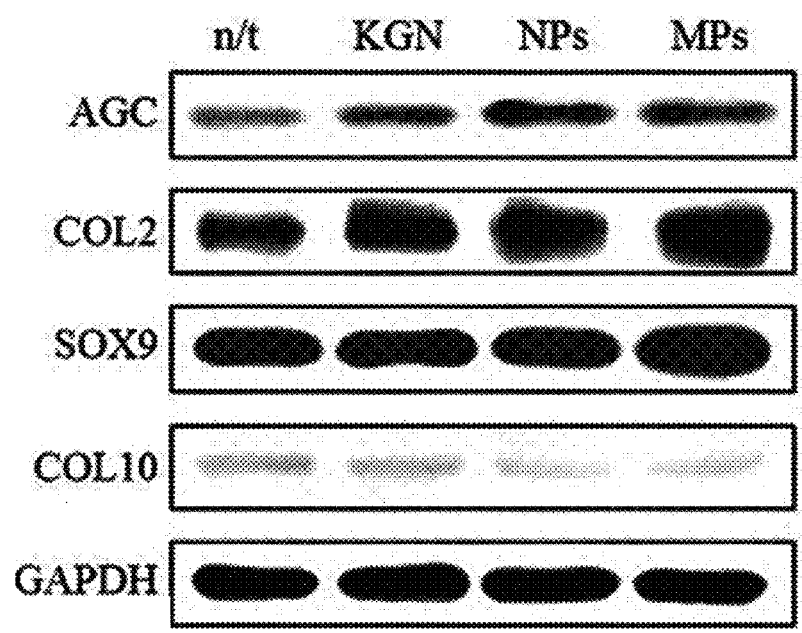
FIG. 9 shows the identification result of changes in expression levels of collagenase type II (COL2), aggrecan (AGC) and collagenage type X (COL10) of groups each treated with kartogenin-chitosan microparticles and kartogenin-chitosan nanoparticles (KGN: a group treated with kartogenin only, CS-KGNNPs: a group treated with kartogenin-chitosan nanoparticles, CS-KGNMPs: a group treated with kartogenin-chitosan microparticles).
Figure 10A:
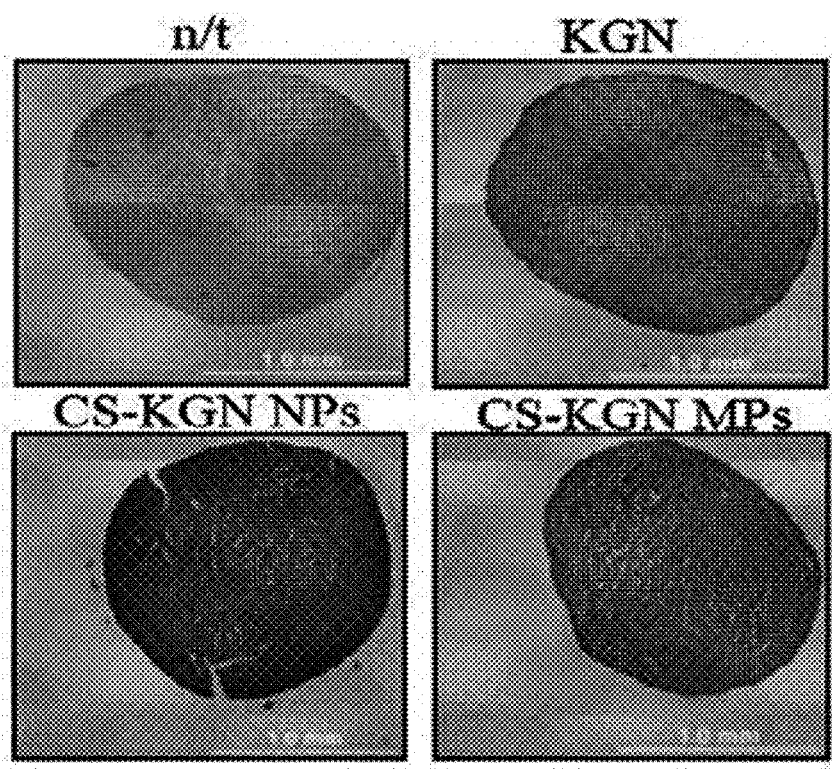
FIG. 10A shows the result of staining chondrogenic differentiation pellet tissues of groups each treated with kartogenin-chitosan microparticles and kartogenin-chitosan nanoparticles with Safranin-O (KGN: a group treated with kartogenin only, CS-KGNNPs: a group treated with kartogenin-chitosan nanoparticles, CS-KGNMPs: a group treated with kartogenin-chitosan microparticles).
Figure 10B:
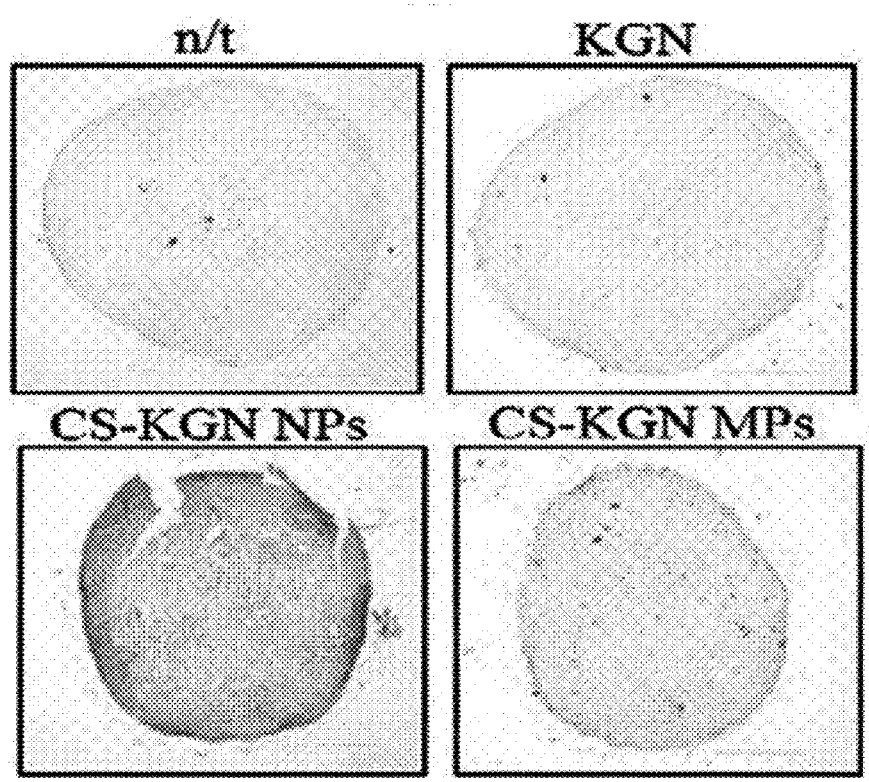
FIG. 10B shows the result of staining chondrogenic differentiation pellet tissues of groups each treated with kartogenin-chitosan microparticles and kartogenin-chitosan nanoparticles with alcian-blue (KGN: a group treated with kartogenin only, CS-KGNNPs: a group treated with kartogenin-chitosan nanoparticles, CS-KGNMPs: a group treated with kartogenin-chitosan microparticles).
Figure 11:
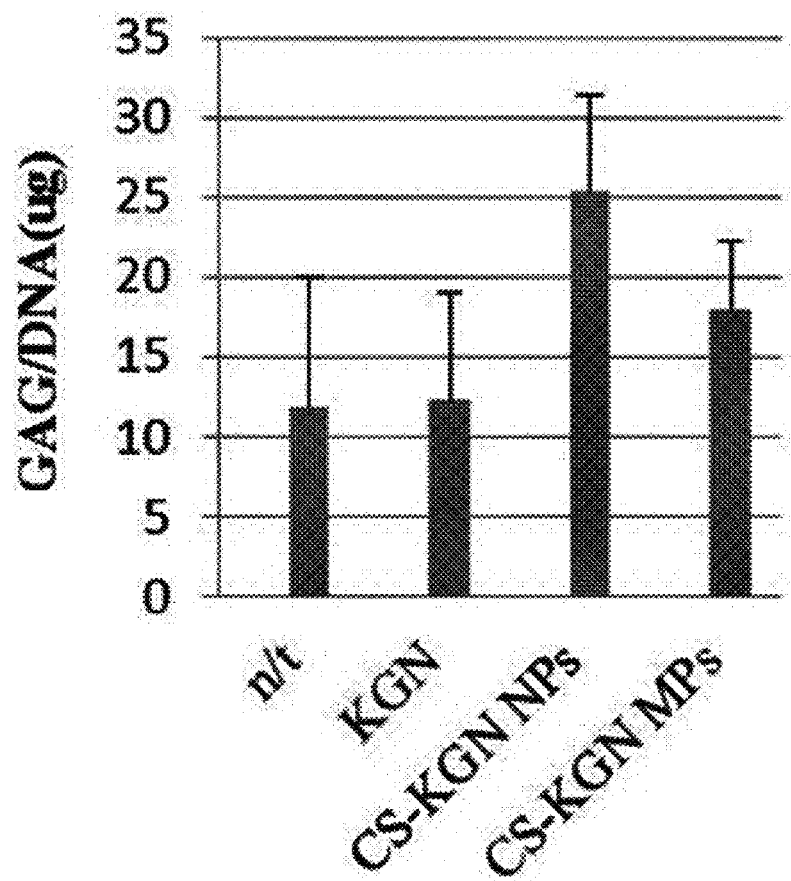
FIG. 11 shows the identification result of GAG contents of groups each treated with kartogenin-chitosan microparticles and kartogenin-chitosan nanoparticles (KGN: a group treated with kartogenin only, CS-KGNNPs: a group treated with kartogenin-chitosan nanoparticles, CS-KGNMPs: a group treated with kartogenin-chitosan microparticles).

Furthermore, as shown in FIG. 9, increases in the expression levels of COL2 and AGC which are chondrogenic differentiation factors and a decrease in the expression level of collagenage type X (COL10) which is a cartilage hypertrophy factor were identified from a group treated with kartogenin-chitosan microparticles or kartogenin-chitosan nanoparticles. Also, as shown in FIGS. 10 and 11, high stainability and GAG content were determined from a group treated with kartogenin-chitosan microparticles or kartogenin-chitosan nanoparticles by staining of chondrogenic differentiation pellet tissues with Safranin-O/alcian-blue.

Accordingly, superior chondrogenic differentiation efficiency of kartogenin-chitosan nano/microparticles was confirmed as compared to kartogenin in a liquid state in the example.

Example 6. Evaluation of Retention Time of Kartogenin-Chitosan Nano/Microparticles in the Joints of Osteoarthritis Animal Model Resection of anterior cruciate ligaments and meniscus removal were performed on rats, and osteoarthritis was induced for 6 weeks. Kartogenin-chitosan micro/nanoparticles were labeled with a fluorescence dye ((FCR-675-carboxylic acid, Flamma™Floursseries, Bioacts), and kartogenin-chitosan microparticles or kartogenin-chitosan nanoparticles each labeled with a fluorescence dye were injected into both knee joints of osteoarthritis model rats. The degree of fluorescence emission was measured using an IVIS-Spectrum measurement system (Xenogen) and quantified to evaluate the retention time in the joints.

Figure 12:
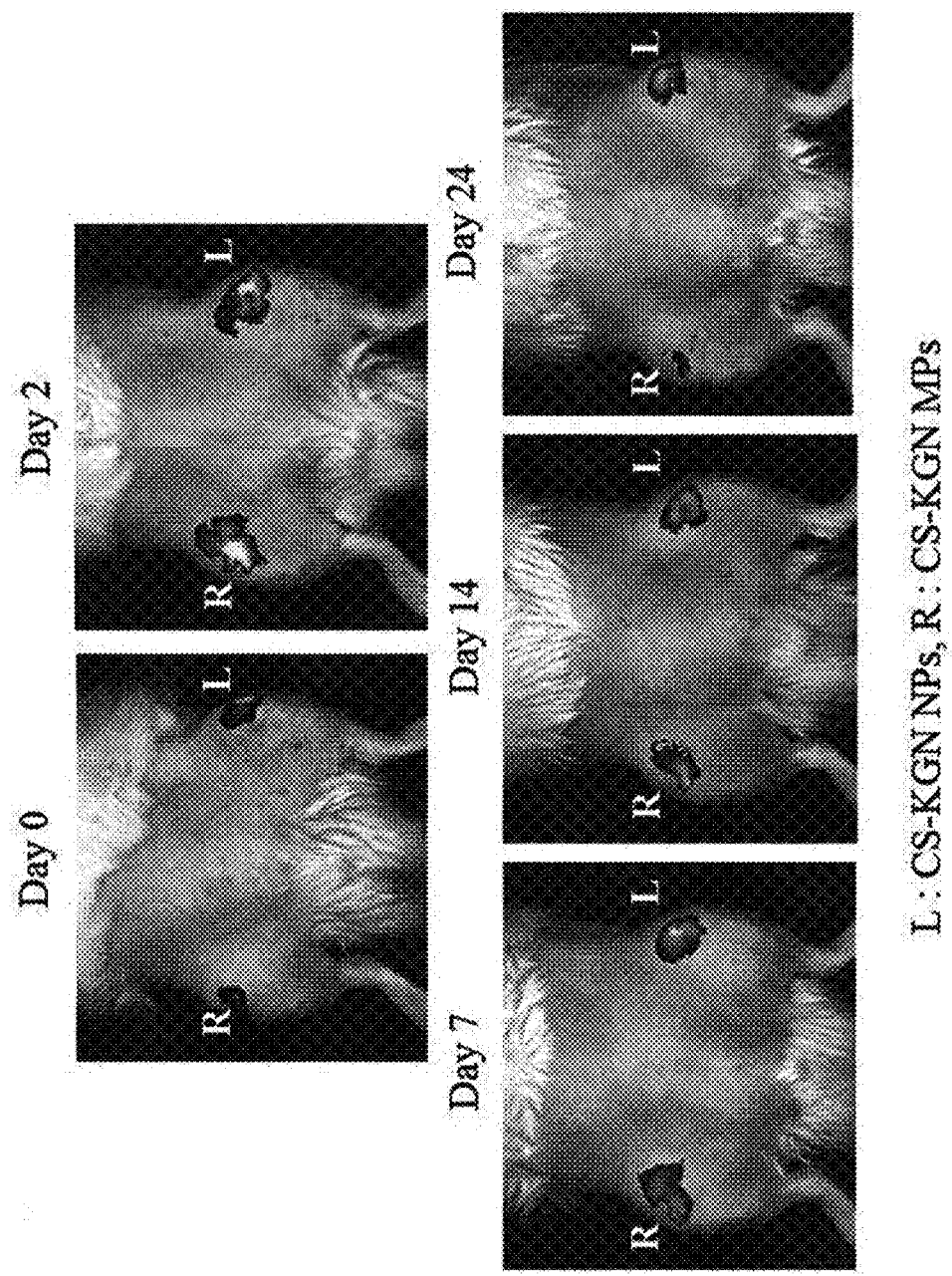
FIG. 12 shows the result of measuring the degree of fluorescence emission after injecting each of fluorescently labeled kartogenin-chitosan microparticles and kartogenin-chitosan nanoparticles into joints of osteoarthritis model rats (CS-KGNNPs: a group treated with kartogenin-chitosan nanoparticles, CS-KGNMPs: a group treated with kartogenin-chitosan microparticles).
Figure 13:
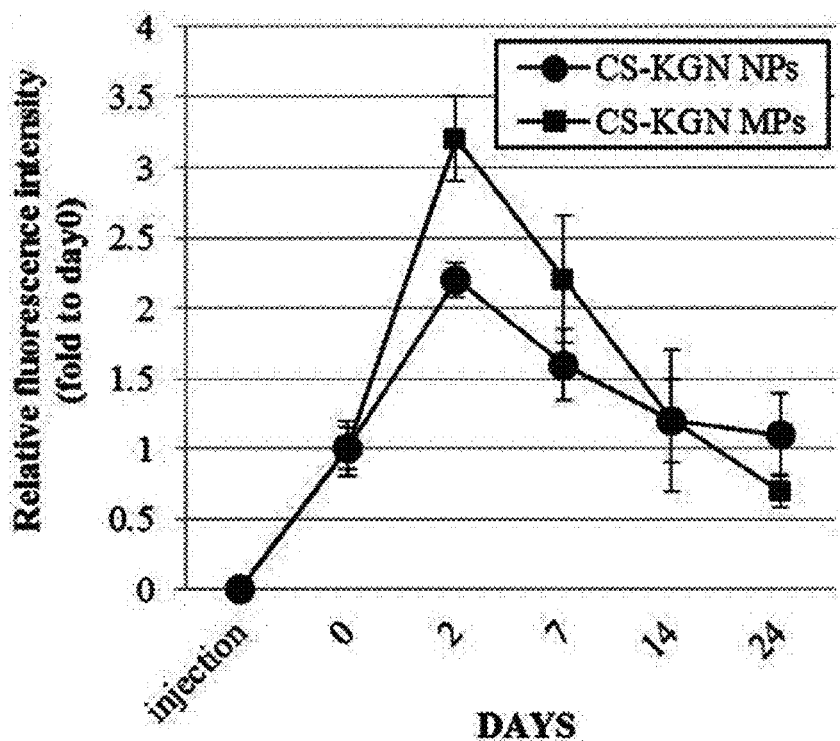
FIG. 13 shows the result of quantifying the degree of fluorescence emission after injecting each of fluorescently labeled kartogenin-chitosan microparticles and kartogenin-chitosan nanoparticles into joints of osteoarthritis model rats (CS-KGNNPs: a group treated with kartogenin-chitosan nanoparticles, CS-KGNMPs: a group treated with kartogenin-chitosan microparticles).

As shown in FIGS. 12 and 13, kartogenin-chitosan microparticles showed a 1.5-times higher residual amount as compared to that of nanoparticles and stayed in the joints for a long period of 2 weeks or more. The residual amount of kartogenin-chitosan nanoparticles was lower than that of microparticles, but the retention time thereof was 3 weeks or more. As a result, as compared to a liquid drug which is quickly dispersed in the joints and has a low effect, the prepared kartogenin-chitosan microparticles or kartogenin-chitosan nanoparticles in the joints exhibited a longer retention time, and thus were determined to be useable as an effective delivery system, as an injectable formulation for intra-articular administration.

Example 7. Evaluation of Osteoarthritis Regeneration after Injection of Kartogenin-Chitosan Nano/Microparticles to Joints of Osteoarthritis Animal Model Resection of anterior cruciate ligaments and meniscus removal were performed on rats, and osteoarthritis was induced for 6 weeks. Kartogenin-chitosan microparticles (2.39 mg) and kartogenin-chitosan nanoparticles (0.215 mg) that can release 25 μM of kartogenin for 3 weeks were suspended in 100 μL of PBS, and were injected into knee joints at 6 weeks and 9 weeks after surgery. The rats were euthanized at 14 weeks, and joint tissues were separated and fixed in 10% paraformaldehyde, and then treated with 6% nitric acid for to decalcification. The tissues were embedded in a Tissue-Tek O.C.T. compound (Sakura Finetek Japan Co., Ltd.), sectioned to 10 μm and attached to a slide glass, and thereafter, staining with Safranin-O/fast green and immunofluorescence of collagen type II (COL2A1) and aggrecan were performed.

Figure 14:
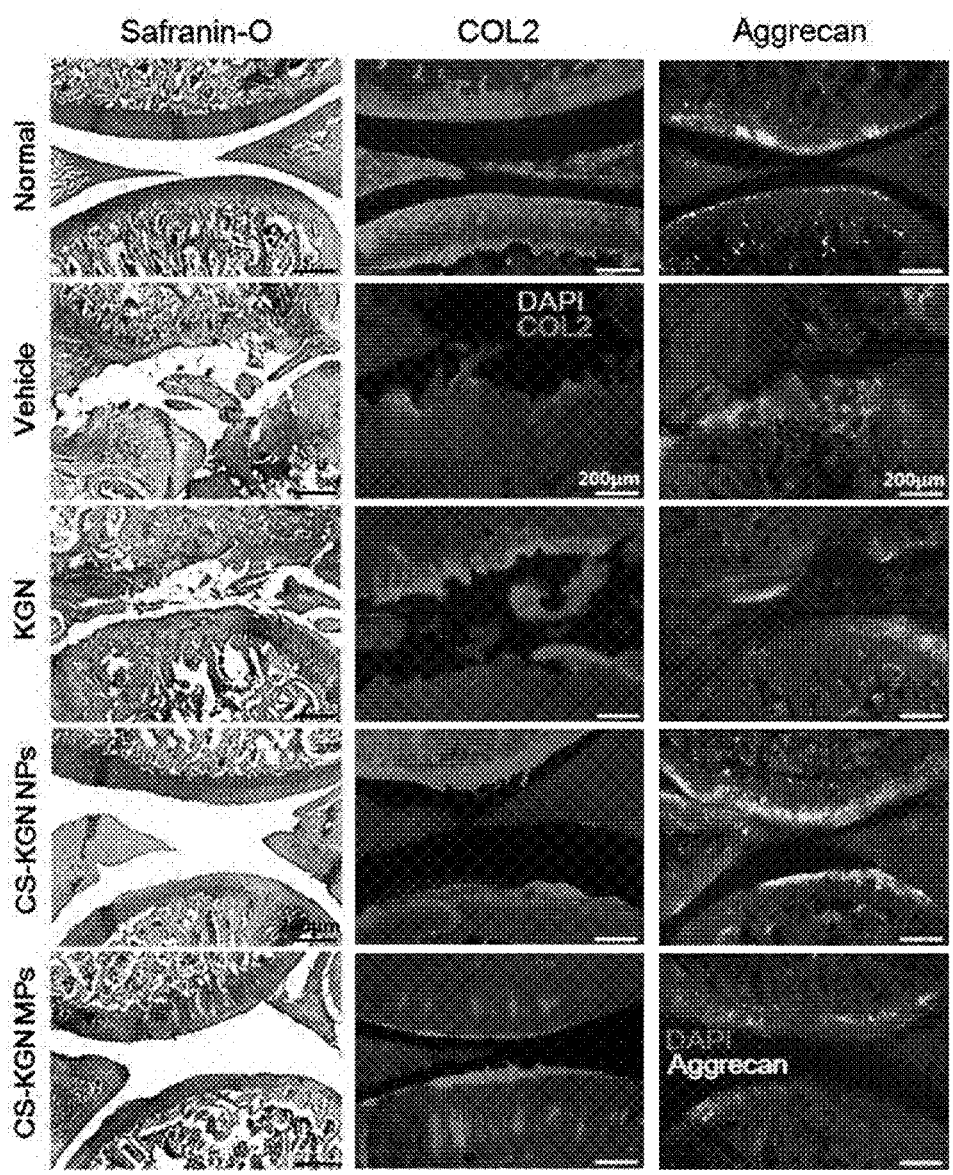
FIG. 14 shows the identification result of proteoglycans localized in cartilage tissues stained with Safranin-O and COL2 and aggrecan which are chondrogenic differentiation factors by immunofluorescent staining analysis when kartogenin-chitosan microparticles and kartogenin-chitosan nanoparticles are injected into knee joints of osteoarthritis model rats (vehicle: a group treated with PBS, KGN: a group treated with kartogenin only, CS-KGNNPs: a group treated with kartogenin-chitosan nanoparticles, CS-KGNMPs: a group treated with kartogenin-chitosan microparticles).

As shown in FIG. 14, a group treated with PBS (vehicle) showed loss of a cartilage matrix, surface peeling and a wide area of cartilage destruction, and a group treated with kartogenin only showed weak vertical matrix cracks in a deep area of cartilage and loss and surface peeling of cartilage, and the staining area of cartilage was reduced as compared to other groups. A group treated with kartogenin-chitosan microparticles or kartogenin-chitosan nanoparticles showed a somewhat damaged area of a cartilage surface, but showed a cartilage surface layer closer to normal than damaged cartilage as compared to a negative control group (normal) in which osteoarthritis was not induced and a group treated with kartogenin only.

Furthermore, as a result of immunofluorescent staining analysis of COL2 and aggrecan which are chondrogenic differentiation factors, a noticeable reduction of COL2 and aggrecan proteins was determined from a group treated with kartogenin only and a group treated with PBS, and increases in COL2 and aggrecan proteins were confirmed from a group treated with kartogenin-chitosan microparticles or kartogenin-chitosan nanoparticles.

Therefore, a group treated with kartogenin-chitosan nano/microparticles was determined to exhibit more excellent effects in cartilage regeneration and inhibition of cartilage loss progression as compared to a group treated with kartogenin only.

The above description of the invention is only exemplary, and it will be understood by those skilled in the art that various modifications can be made without departing from the scope of the present invention and without changing essential features. Therefore, the above-described examples should be considered in a descriptive sense only and not for purposes of limitation.

The invention claimed is:

1. A kartogenin-conjugated chitosan particle, formed by a covalent bond between kartogenin which is a hydrophobic compound and chitosan which is a hydrophilic compound.

2. The kartogenin-conjugated chitosan particle according to claim 1, wherein the covalent bond is a peptide bond.

3. The kartogenin-conjugated chitosan particle according to claim 1, wherein the composite particle is in the form of a nanoparticle or a microparticle.

4. A pharmaceutical composition for preventing or treating a bone disease, comprising the kartogenin-conjugated chitosan particle according to claim 1.

5. The pharmaceutical composition according to claim 4, wherein the bone disease is osteoarthritis.

6. The pharmaceutical composition according to claim 4, wherein the composition is an injectable formulation for intra-articular administration.

7. A method of preventing or treating a bone disease, comprising a step of administering the kartogenin-conjugated chitosan particle according to claim 1 to a subject.

* * * * *